(12) United States Patent
Bendik et al.

(10) Patent No.: US 10,336,675 B2
(45) Date of Patent: Jul. 2, 2019

(54) BIAROMATIC VITAMIN D ANALOGS

(71) Applicant: DSM IP ASSETS B.V., Heerlen (NL)

(72) Inventors: Igor Bendik, Kaiseraugst (CH); Piero Geotti-Bianchini, Kaiseraugst (CH); Marc Heidl, Kaiseraugst (CH); Eileen Jackson, Kaiseraugst (CH); Alexander Schlifke-Poschalko, Kaiseraugst (CH)

(73) Assignee: DSM IP ASSETS B.V., Heerlen (NL)

( * ) Notice: Subject to any disclaimer, the term of this patent is extended or adjusted under 35 U.S.C. 154(b) by 0 days.

(21) Appl. No.: 16/061,697

(22) PCT Filed: Dec. 14, 2016

(86) PCT No.: PCT/EP2016/080891
§ 371 (c)(1),
(2) Date: Jun. 13, 2018

(87) PCT Pub. No.: WO2017/102790
PCT Pub. Date: Jun. 22, 2017

(65) Prior Publication Data
US 2019/0002378 A1    Jan. 3, 2019

(30) Foreign Application Priority Data

Dec. 18, 2015  (EP) .................................... 15201109

(51) Int. Cl.
| | | |
|---|---|---|
| *A61K 31/045* | (2006.01) | |
| *C07C 33/28* | (2006.01) | |
| *A61K 8/34* | (2006.01) | |
| *A61K 8/67* | (2006.01) | |
| *A61Q 19/00* | (2006.01) | |
| *C07C 33/48* | (2006.01) | |
| *A61Q 19/08* | (2006.01) | |

(52) U.S. Cl.
CPC .............. *C07C 33/28* (2013.01); *A61K 8/345* (2013.01); *A61K 8/67* (2013.01); *A61Q 19/00* (2013.01); *A61Q 19/08* (2013.01); *C07C 33/486* (2013.01)

(58) Field of Classification Search
CPC ....... C07C 33/28; C07C 33/486; A61Q 19/08; A61Q 19/00; A61P 17/00; A61K 8/67; A61K 8/345
USPC ........................................................ 514/730
See application file for complete search history.

(56) References Cited

U.S. PATENT DOCUMENTS

2004/0224929 A1    11/2004   Bernardon

FOREIGN PATENT DOCUMENTS

| | | |
|---|---|---|
| FR | 2 862 540 | 5/2005 |
| WO | 2000/026167 | 5/2000 |
| WO | 2002/094754 | 11/2002 |
| WO | 2005/053666 | 6/2005 |

OTHER PUBLICATIONS

International Search Report for PCT/EP2016/080891, dated Jan. 26, 2017, 5 pages.
Written Opinion of the ISA for PCT/EP2016/080891, dated Jan. 26, 2017, 6 pages.

*Primary Examiner* — Taylor V Oh
(74) *Attorney, Agent, or Firm* — Nixon & Vanderhye P.C.

(57) ABSTRACT

Novel biaromatic compounds, which are vitamin D analogs, processes for their preparation and cosmetic, dermatological and pharmaceutical preparations containing one or more of these compounds.

16 Claims, No Drawings

BIAROMATIC VITAMIN D ANALOGS

This application is the U.S. national phase of International Application No. PCT/EP2016/080891 filed Dec. 14, 2016, which designated the U.S. and claims priority to EP Patent Application No. 15201109.4 filed Dec. 18, 2015, the entire contents of each of which are hereby incorporated by reference.

The present invention relates to novel biaromatic compounds, which are vitamin D analogs. The invention furthermore relates to processes for their preparation and cosmetic, dermatological and pharmaceutical preparations containing one or more of these compounds.

Vitamin D comprises a group of fat-soluble compounds, which are e.g. essential for maintaining the calcium and phosphate balance in the body, build and maintain healthy bones, control cell division and specialization and modulate the immune system.

The European Food Safety Authority (EFSA) has confirmed that health benefits have been established for the dietary intake of vitamin D:
  Vitamin D contributes to the normal function of the immune system.
  Vitamin D contributes to normal development of bones and teeth.
  Vitamin D may reduce the risk of falling. Falling is a risk factor for bone fractures.
  A relationship was established between the intake of calcium, either alone or in combination with vitamin D, and reducing the loss of BMD, which may contribute to a reduction in the risk of bone fracture.
  A relationship has been established between the dietary intake of vitamin D and a contribution to a normal function of the immune system and inflammatory response, maintenance of normal muscle function and maintenance of normal cardiovascular function. The target population is assumed to be general population.
  Calcium and vitamin D are needed for the maintenance of normal bone.
  A relationship has been established between the dietary intake of vitamin D and maintenance of normal bone and teeth, absorption and utilization of calcium and phosphorus and normal blood calcium concentrations, and normal cell division.
  Vitamin D is needed for normal growth and development of bone in children.
  Calcium and vitamin D may reduce the loss of bone mineral in post-menopausal women. Low bone mineral density is a risk factor in the development of osteoporotic bone fractures.

Furthermore, some studies have indicated that vitamin D may have anti-cancer effects and that vitamin D deficiency or a low vitamin D status may be linked to an increased risk of developing autoimmune diseases, overactive immune responses of the body attacking its own cells and organs. The breadth and magnitude of vitamin D activity suggest potential for the treatment of several diseases and disorders.

Newly developed vitamin D analogues have also been shown to have many therapeutic properties of vitamin D and several have been or are being tested in preclinical and clinical trials for the treatment of various types of cancer and osteoporosis as well as immunosuppression.

US 2004/0224929 A1 describes vitamin D analogs, which show biological activity, but the disclosure of this document could not direct the person skilled in the art to the current invention.

It has now surprisingly been found that the new compounds according to formula (I)

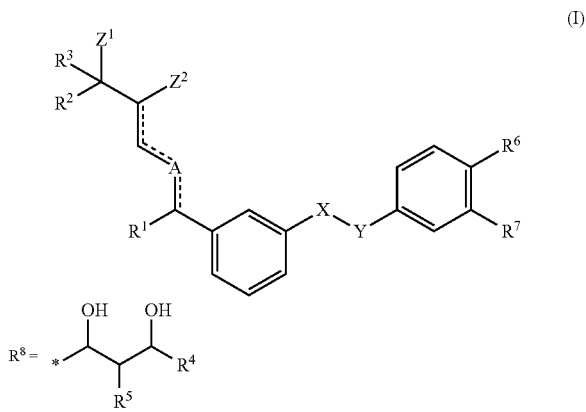

wherein
  X and Y, are either both —$CH_2$—, or one of X and Y is —$CH_2$— and the other one is —O—; and
  $R^1$ is a methyl group or an ethyl group; and
  A is either carbon or oxygen; and
  one of $Z^1$ and $Z^2$ represents a hydroxyl group and the other one is a hydrogen atom; and
  $R^2$ and $R^3$, independently of each other, represent a hydrogen atom, a methyl group, an ethyl group, or a $CF_3$ group or $R^2$ and $R^3$, together with the carbon they are bound to, form a cyclopropyl group; and
  wherein the dotted/solid lines ( ------ ) represent either a single carbon-carbon bond or a double carbon-carbon bond, with the proviso that, if two of said bonds are double bonds, these bonds are conjugated; and
  one of $R^6$ and $R^7$ represents a hydrogen atom and the other one represents a radical $R^8$, wherein
    $R^4$ represents a hydrogen atom, a methyl group, an ethyl group, a propyl group, a $(CH_2)_nOR^9$ group where n is 1, 2, 3 or 4; and $R^5$ represents a hydrogen atom, a methyl group, an ethyl group, a propyl group, or a $(CH_2)_nOR^{10}$ group where n is 1, 2 or 3, wherein $R^9$ and $R^{10}$, independently of each other, represent a hydrogen atom, a methyl group, or an ethyl group;
are highly efficient in cosmetic, dermatological and pharmaceutical applications.

Particularly preferred compounds in all embodiments according to the present invention are compounds of formula (I), wherein $R^1$ is ethyl.

Furthermore preferred are compounds of formula (I), wherein A is carbon, further preferred wherein A is carbon and two of the dotted/solid lines are conjugated double bonds.

It is furthermore preferred that $Z^2$ represents the hydroxyl group, if $R^2$ and $R^3$, together with the carbon they are bound to, form a cyclopropyl group.

Furthermore preferred are compounds of formula (I), wherein $R^2$, $R^3$ independently of each other represent an ethyl group, or a $CF_3$ group.

Furthermore preferred are compounds of formula (I), wherein $R^4$ and $R^5$ are different and represent a hydrogen atom and a methyl group.

Especially preferred are compounds of formula (I), wherein $R^2$, $R^3$ are independently of each other selected from ethyl or trifluoromethyl and R⁴ and R⁵ are different and represent a hydrogen atom and a methyl group.

It is well understood, that the present invention encompasses (if applicable) the compounds according to the present invention as optically pure isomers, such as e.g. pure enantiomers, or as mixture of different isomers, such as e.g. racemates.

The present invention furthermore relates to the processes for preparation of the compounds indicated above.

Particularly preferred compounds for all embodiments according to the present invention are the compounds according to the formulas I-a, I-b, I-c, I-d I-e and/or I-f, as listed in the following:

(I-a)

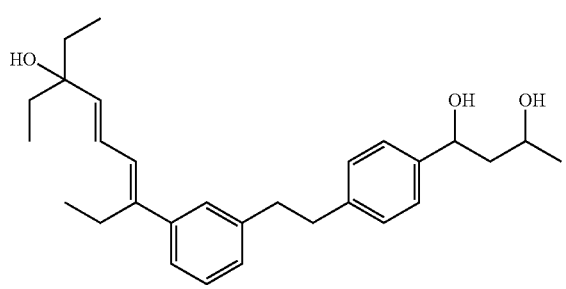

1-(4-(3-((3E,5E)-7-ethyl-7-hydroxynona-3,5-dien-3-yl)phenethyl)-phenyl)butane-1,3-diol (I-b)

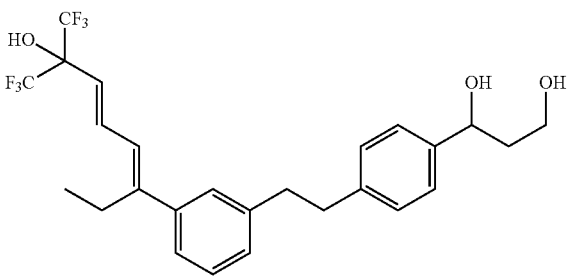

1-(4-(3-((3E,5E)-8,8,8-trifluoro-7-hydroxy-7-(trifluoromethyl)octa-3,5-dien-3-yl)phenethyl)phenyl)propane-1,3-diol (I-c)

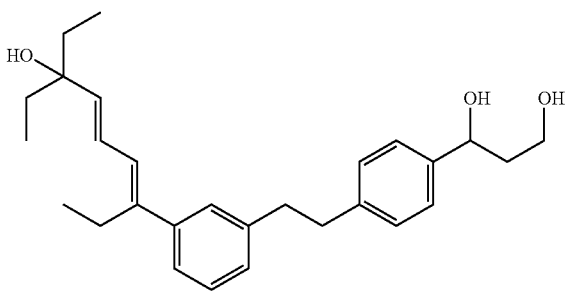

1-(4-(3-((3E,5E)-7-ethyl-7-hydroxynona-3,5-dien-3-yl)phenethyl)-phenyl)propane-1,3-diol (I-d)

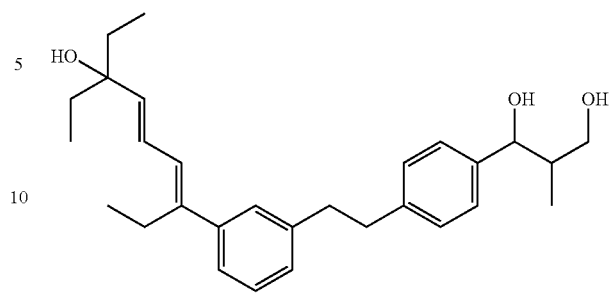

1-(4-(3-((3E,5E)-7-ethyl-7-hydroxynona-3,5-dien-3-yl)phenethyl)-phenyl)-2-methylpropane-1,3-diol (I-e)

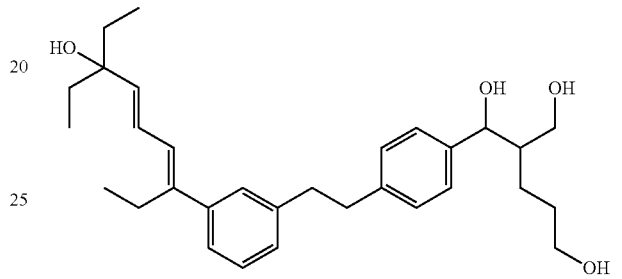

1-(4-(3-((3E,5E)-7-ethyl-7-hydroxynona-3,5-dien-3-yl)phenethyl)-phenyl)-2-(hydroxymethyl)pentane-1,5-diol (I-f)

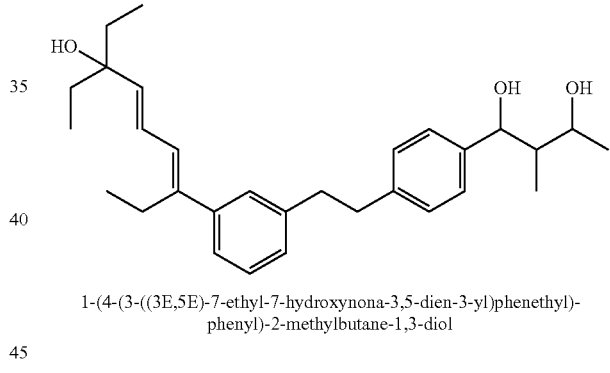

1-(4-(3-((3E,5E)-7-ethyl-7-hydroxynona-3,5-dien-3-yl)phenethyl)-phenyl)-2-methylbutane-1,3-diol The compounds according to the invention have biological properties analogous to those of vitamin D, especially the properties of transactivation of vitamin D response elements (VDRE), such as an agonist activity with respect to receptors of vitamin D or of its derivatives. Vitamins D or their derivatives are understood as meaning, for example, the derivatives of vitamin D2 or D3 and in particular 1,25-dihydroxy-vitamin D3 (calcitriol).

This agonist activity with respect to vitamin D receptors or its derivatives can be demonstrated in vitro by methods recognized in the field of the study of gene transcription (Hansen et al., The Society For Investigative Dermatologie, vol. 1, No 1, April 1996).

By way of example, the human vitamin D receptor (VDR) agonist activity of the claimed compounds can be tested using a cell based transactivation assay in an eukaryotic cell line. After a co-transfection, using a reporter plasmid construct and a hybrid receptor construct containing the ligand-binding domain of the human VDR linked to the DNA-binding domain of the yeast transcription factor GAL4, the cultured cells were stimulated by the VDR agonists. The hybrid VDR-GAL4 receptor binds the VDR agonists and transactivates luciferase reporter expression through the GAL4-response elements in the promoter of the luciferase gene (reporter construct). The VDR agonist binding and transactivation is determined by measuring the luciferase luminescence activity. The effective concentration of half maximal activation ($EC_{50}$) was determined for the VDR agonists by means of dose-response experiments. The details of the protocol method of this test according to the invention are described in the example section.

The compounds according to the invention have a marked activity in the field of cell proliferation and/or differentiation and in the field of hyperproliferation of tissues of ectodermal origin (skin, epithelium, etc.), whether benign or malignant. They can for example advantageously be used to support wound healing. The compounds according to the invention can furthermore be used to combat age-associated impairments in dermal integrity, i.e. to soften signs of skin aging (for example wrinkles or fine lines), whether photoinduced or chronological and/or to treat cicatrization disorders. They are furthermore particularly highly suitable in the following fields of treatment:

dermatological complaints linked to a keratinization disorder having a bearing on differentiation and proliferation such as common acne, blackheads, polymorphs, rosacea, nodulocystic acne, acne conglobata, senile acne, secondary acne such as solar, medicinal or professional acne;

dermatological complaints with an inflammatory and/or immunoallergic component, with or without cell proliferation disorder, and such as all forms of psoriasis, whether it be cutaneous, mucous or ungual, and even psoriatic rheumatism, or else cutaneous atopy, such as eczema or respiratory atopy or else gingival hypertrophy;

dermatological or general complaints with an immunological component; actopic dermatitis; psoriasis;

sebaceous function disorders such as hyper-seborrhea of acne or simple seborrhea;

cutaneous disorders due to exposure to UV rays, aging of the skin, whether it be photoinduced or chronological, pigmentations and actinic keratoses, or any pathologies associated with chronological or actinic aging;

cicatrization disorders or stretch marks, treatment of xerotic skin;

inflammatory complaints such as arthritis, complaints of viral origin at the cutaneous or general level, such as Kaposi's syndrome;

ophthalmological complaints, especially corneopathy;

cancerous or precancerous states of cancers having or being able to be induced by vitamin D receptors, such as breast cancer, leukemia, myelodysplasic syndromes and lymphomas, carcinomas of the cells of the malpighian epithelium and gastrointestinal cancers, melanomas, and osteosarcoma;

disorders related to hair follicle functions, such as alopecia of different origins, especially alopecia due to chemotherapy or to radiation;

immune complaints, such as autoimmune diseases, diabetes mellitus of type 1, multiple sclerosis, lupus and lupus-type complaints, asthma, glomerulonephritis; selective dysfunctions of the immune system, such as AIDS, tuberculosis, immune rejection; immune modulation disorders, such as in case of innate immunity deficits, upper respiratory tract infections, influenza, skin allergies;

deficiencies in vitamin D and other complaints of the homeostasis of minerals in the plasma and the bones, such as rachitis, vitamin D resistant rickets, osteomalacia, osteoarthritis, osteoporosis, especially in the case of menopausal women, renal osteodystrophia, or complaints of the parathyroid function; muscle aches and weakness related disorders, such as sarcopenia and falling;

complaints of the cardiovascular system such as arteriosclerosis, hypertension, lung function or myocardial infarction; as well as non-insulin-dependent diabetes and cognition related deficits, such as dementia and Alzheimer.

The compounds according to the invention are particularly suited for the treatment of age-associated impairments in dermal integrity and wound healing. They can advantageously be used in the cosmetic field, in particular in products for body and hair hygiene and especially in skin (including face) care products. These products may e.g. be useful in the treatment of skin with a tendency to acne, to combat the greasy aspect of skin and/or hair, in protection against the harmful effects of the sun or in the treatment of physiologically dry skin. They can be used to prevent (photo)age-induced skin structure and function defects, photoinduced or chronological aging and symptoms associated herewith, such as skin thinning, wrinkle formation and fine lines.

Thus, the invention also relates to a method to smoothen wrinkles and/or fine lines and/or to decrease their volume and depth, said method comprising the step of applying a cosmetic composition according to the present invention with all the definitions and preferences given herein to the affected area.

The term 'cosmetic composition' refers to compositions which are used to treat, care for or improve the appearance of the skin and/or the scalp. Particular advantageous cosmetic compositions are skin and/or face care compositions.

The cosmetic compositions according to the invention (i.e. compositions containing at least one compound according to the invention) are preferably intended for topical application, which is to be understood as the external application to keratinous substances, such as in particular the skin.

The cosmetic compositions of the present invention can be formulated as a wide variety of product types, including creams, waxes, pastes, ointments, lotions, milks, mousses, gels, oils, tonics, aerosols and sprays. Preferably the compounds of formula (I) are formulated into lotions, creams, gels, and sprays. These product forms may be used for a number of applications, including, but not limited to, hand and body lotions, face creams, facial moisturizers, anti-ageing preparations, make-ups including foundations, and the like. Any additional components required to formulate such products vary by product type and can be routinely chosen by the person skilled in the art.

The amount of the compound of formula (I) in the cosmetic composition according to the present invention is at least 0.1 ppm (0.00001 wt.-%) based on the total weight of the cosmetic composition. In all embodiments of the present invention the amount of the compound of formula (I) is preferably selected in the range of about 0.00001 to 0.5 wt.-%, more preferably in the range of 0.00001 to 0.1 wt.-%, most preferably in the range of 0.0001 to 0.1 wt.-% based on the total weight of the cosmetic composition. The amount of the compound of formula (I) can be adjusted by a person skilled in the art in order to achieve the desired beneficial effect.

The cosmetic compositions according to the present invention can be prepared by conventional methods, such as e.g. by admixing a compound of formula (I) with a cosmetically acceptable carrier.

The term 'cosmetically acceptable carrier' as used herein refers to a physiologically acceptable medium which is compatible with keratinous substances. Suitable carriers (also known as "cosmetic bases" or "cosmetic base formulations") are well known in the art and are selected based on the (end-use) application. Preferably, the carriers of the present invention are suitable for application to skin and constitute e.g. creams, milks, lotions, ointments, solutions, sprays, masks, serums, hydrodispersions, foundations, creamgels, gels etc. Such carriers are well-known to the person of ordinary skill, and can preferably include one or more cosmetic carrier oil(s) and other cosmetic ingredients to produce a wide variety of skincare products.

Accordingly, the cosmetic compositions of the invention (including the carrier) may include both water soluble ingredients and oil soluble ingredients and can comprise conventional cosmetic adjuvants and additives, such as water, fatty substances, (essential) oils, waxes, organic solvents, preservatives/antioxidants, stabilizers, silicones, thickeners, softeners, emulsifiers, antifoaming agents, aesthetic components (such as fragrances), surfactants, anionic, cationic, nonionic or amphoteric polymers or mixtures thereof, propellants, acidifying or basifying agents, dyes, colorings/colorants, abrasives, absorbents, chelating agents and/or sequestering agents, liquid or solid fillers, diluents, excipients, astringents, pigments or any other ingredients usually formulated into such compositions.

In accordance with the present invention, the cosmetic compositions according to the invention may also comprise additional cosmetically active ingredients conventionally used in a cosmetic composition, such as especially: wetting agents; depigmenting agents, such as hydroquinone, azelaic acid, caffeic acid or kojic acid; emollients; hydrating agents, such as glycerol, PEG 400, thiamorpholinone and its derivatives or urea; antifungal agents, such as ketoconazole or the polymethylene-4,5-isothiazolin-3-ones; agents favoring the regrowth of the hair, such as minoxidil (2,4-di-amino-6-piperidinopyrimidine 3-oxide) and its derivatives, diazoxide (7-chloro-3-methyl-1,2,4-benzo-thiadiazine 1,1-dioxide) and phenytoin (5,5-diphenyl-imidazolidine-2,4-dione); non-steroidal anti-inflammatory agents; carotenoids, especially beta-carotene;

Exemplary active ingredients furthermore encompass skin lightening agents; UV-filters; agents for the treatment of hyperpigmentation; agents for the prevention or reduction of inflammation; firming, moisturizing, soothing, and/or energizing agents as well as agents to improve elasticity and skin barrier.

The cosmetically active ingredients useful herein can in some instances provide more than one benefit, or operate via more than one mode of action.

The (one or more) compound(s) according to the invention can furthermore be advantageously used in combination with retinoids, in association with antioxidants, with alpha-hydroxy- or alpha-keto acids or their derivatives, or else with ion channel blockers. Preferred alpha-hydroxy- or alpha-keto acids or their derivatives according to the invention are, for example, lactic acid, malic acid, citric acid, glycolic acid, mandelic acid, tartaric acid, glyceric acid, ascorbic acid, as well as their salts, amides and/or esters.

Examples of cosmetic excipients, diluents, adjuvants, additives as well as active ingredients commonly used in the skin care industry which are suitable for use in the cosmetic compositions of the present invention are for example described in the International Cosmetic Ingredient Dictionary & Handbook by Personal Care Product Council (http://www.personalcarecouncil.org/), accessible by the online INFO BASE (http://online.personalcarecouncil.org/jsp/Home.jsp), without being limited thereto.

The necessary amounts of the active ingredients as well as the cosmetic excipients, diluents, adjuvants, additives etc. can, based on the desired product form and application, easily be determined by the skilled person. The additional ingredients can either be added to the oily phase, the aqueous phase or separately as deemed appropriate.

Of course, the person skilled in this art will take care to select the above mentioned optional additional ingredients and their amounts such that the advantageous effects of the compound(s) according to the invention are not, or not substantially, detrimentally affected by the envisaged addition or additions.

Dermatological compositions containing at least one compound according to the invention are also advantageous and are intended for the treatment of the skin and/or the treatment of the mucous membranes. They can be present in the form of salves, creams, milks, ointments, powders, moistened swabs, solutions, gels, sprays, lotions or suspensions or in the form patches and/or hydrogels or other dosage forms allowing controlled release.

Dermatological compositions as described above contain one or more compound(s) according to the invention in a concentration of between 0.00001 to 2 wt.-%, preferably between 0.0001 to 1 wt.-%, based on to the total weight of the composition, depending on the clinical indication.

In accordance with the present invention, the dermatological compositions according to the invention may also comprise additional dermatologically active ingredients conventionally used in a dermatological composition, such as especially antiseborrheic or antiacne agents, such as S-carboxymethylcysteine, S-benzylcysteamine, their salts and their derivatives, or benzoyl peroxide; corticosteroids; antipsoriatic agents, such as anthralin and its derivatives and finally eicoesters and amides.

The cosmetic or dermatological compositions according to the present invention may be in the form of a suspension or dispersion in solvents or fatty substances, or alternatively in the form of an emulsion or micro-emulsion (in particular of oil-in-water (O/W) or water-in-oil (W/O) type, silicone-in-water (Si/W) or water-in-silicone (W/Si) type, PIT-emulsion, multiple emulsion (e.g. oil-in-water-in oil (O/W/O) or water-in-oil-in-water (W/O/W) type), pickering emulsion, hydrogel, alcoholic gel, lipogel, one- or multiphase solution or vesicular dispersion or other usual forms, which can also be applied by pens, as masks or as sprays.

If the composition is an emulsion, such as in particular an O/W, W/O, Si/W, W/Si, O/W/O, W/O/W multiple or a pickering emulsion, then the amount of the oil phase present in such cosmetic emulsions is preferably at least 10 wt.-%, such as in the range of 10 to 60 wt.-%, preferably in the range of 15 to 50 wt.-%, most preferably in the range of 15 to 40 wt.-%, based on the total weight of the cosmetic composition.

In one preferred embodiment, the composition according to the present invention is in the form of an oil-in-water (O/W) emulsion comprising an oily phase dispersed in an aqueous phase in the presence of an O/W emulsifier. The preparation of such O/W emulsions is well known to a person skilled in the art.

If the composition according to the invention is an O/W emulsion, then it contains advantageously at least one O/W- or Si/W-emulsifier selected from the list of glyceryl stearate citrate, glyceryl stearate SE (self-emulsifying), stearic acid, salts of stearic acid, polyglyceryl-3-methylglycosedistearate. Further suitable emulsifiers are phosphate esters and the salts thereof, such as cetyl phosphate (e.g. as Amphisol® A from DSM Nutritional Products Ltd.), diethanolamine cetyl phosphate (e.g. as Amphisol® DEA from DSM Nutritional Products Ltd.), potassium cetyl phosphate (e.g. as Amphisol® K from DSM Nutritional Products Ltd.), sodium cetearylsulfate, sodium glyceryl oleate phosphate, hydrogenated vegetable glycerides phosphate and mixtures thereof. Further suitable emulsifiers are sorbitan oleate, sorbitan sesquioleate, sorbitan isostearate, sorbitan trioleate, cetearyl glucoside, lauryl glucoside, decyl glucoside, sodium stearoyl glutamate, sucrose polystearate and hydrated polyisobutene. Furthermore, one or more synthetic polymers may be used as an emulsifier. For example, PVP eicosene copolymer, acrylates/C10-30 alkyl acrylate crosspolymer, and mixtures thereof.

The at least one O/W, respectively Si/W emulsifier is preferably used in an amount of 0.5 to 10 wt. %, in particular in the range of 0.5 to 6 wt.-%, more preferably in the range of 0.5 to 5 wt.-%, most preferred in the range of 1 to 4 wt.-%, based on the total weight of the cosmetic composition.

Particular suitable O/W emulsifiers to be used in the cosmetic compositions according to the invention encompass phosphate ester emulsifiers, such as advantageously 8-10 alkyl ethyl phosphate, C9-15 alkyl phosphate, ceteareth-2 phosphate, ceteareth-5 phosphate, ceteth-8 phosphate, ceteth-10 phosphate, cetyl phosphate, C6-10 pareth-4 phosphate, C12-15 pareth-2 phosphate, C12-15 pareth-3 phosphate, DEA-ceteareth-2 phosphate, DEA-cetyl phosphate, DEA-oleth-3 phosphate, potassium cetyl phosphate, deceth-4 phosphate, deceth-6 phosphate and trilaureth-4 phosphate.

A particular suitable O/W emulsifier to be used in a cosmetic compositions according to the invention is potassium cetyl phosphate, e.g. commercially available as Amphisol® K at DSM Nutritional Products Ltd Kaiseraugst.

Another particular suitable class of O/W emulsifiers are non-ionic self-emulsifying systems derived from olive oil, e.g. known as (INCI Name) cetearyl olivate and sorbitan olivate (chemical composition: sorbitan ester and cetearyl ester of olive oil fatty acids), sold under the tradename OLIVEM 1000.

In one particular embodiment, the invention relates to cosmetic compositions with all the definitions and preferences given herein in the form of O/W emulsions comprising an oil phase dispersed in an aqueous phase in the presence of an O/W emulsifier, wherein the O/W emulsifier is potassium cetyl phosphate. The amount of oily phase in such O/W emulsions is preferably at least 10 wt.-%, more preferably in the range of 10 to 60 wt.-%, most preferably in the range of 15 to 50 wt.-%, such as in the range of 15 to 40 wt.-%.

Cosmetic and dermatological compositions according to the invention in general have a pH in the range of 3 to 10, preferably a pH in the range of 4 to 8 and most preferably a pH in the range of 4 to 7.5. The pH can easily be adjusted as desired with suitable acids, such as e.g. citric acid, or bases, such as sodium hydroxide (e.g. as aqueous solution), triethanolamine (TEA Care), Tromethamine (Trizma Base) and Aminomethyl Propanol (AMP-Ultra PC 2000), according to standard methods in the art.

The amount of the cosmetic composition to be applied to the skin is not critical and can easily be adjusted by a person skilled in the art. Preferably, the amount is selected in the range of 0.1 to 3 mg/cm$^2$ skin, such as preferably in the range of 0.1 to 2 mg/cm$^2$ skin and most preferably in the range of 0.5 to 2 mg/cm$^2$ skin.

In other embodiments the invention encompasses a pharmaceutical composition comprising one or more compounds according to the present invention.

The invention is further illustrated with reference to the following, non-limiting examples, in which all percentages are by weight based on total weight unless otherwise specified.

EXAMPLES

Instruments and Materials

Analytical chromatograms were measured on a Waters Acquity Ultra Performance Liquid Chromatography, equipped with an Acquity HSS T3 100 Å, 1.8 µm 2.1×50 mm$^2$ analytical column and a PDA detector operating in the 200-400 nm wavelength range. H$_2$O+0.02% TFA (A phase) and MeCN+0.02% TFA (B phase) were used as eluents with a flow of 0.5 mL/min.

Low-resolution mass-spectra were measured on a Waters Acquity I-Class Ultra Performance Liquid Chromatography, equipped with an Acquity HSS T3 100 Å, 1.8 µm 2.1×50 mm$^2$ analytical column and a PDA detector operating in the 200-400 nm wavelength range coupled to a Waters Single Quadrupole Detector mass spectrometer operating in positive electrospray ionization (ESI+) mode and detecting in the m/z range 100-1500. H$_2$O+0.04% HCOOH (A' phase) and MeCN+0.04% HCOOH (B' phase) were used as eluents with a flow of 0.6 mL/min.

Preparative purifications on reverse phase were performed on a Waters High Performance Liquid Chromatography LC-2525 equipped with a Waters 2767 Sample Manager and a Waters FCII automated fraction collector, using a Grom Saphir 110 C18 10 µm 50×300 mm$^2$ preparative column and a Waters 2487 double wavelength UV-Vis detector operating at 220 and 254 nm.

H$_2$O+0.07% TFA (A" phase) and MeCN+0.07% TFA (B" phase) were used as eluents with a flow of 55 mL/min.

Silica gel 60 (0.040-0.063 mm, Merck) was used as stationary phase for flash-chromatographic purifications.

Nuclear magnetic resonance spectra were recorded on a Bruker Avance 300 spectrometer equipped with 5 mm BBO BB-1H probe head operating at 300 MHz for $^1$H and 75.5 MHz for $^{13}$C. Spectra were recorded in deuterochlorophorm (CDCl$_3$) or perdeuterated methyl sulfoxide (d$_6$-DMSO) and were referenced to the residual solvent signal (CDCl$_3$: 7.26 ppm, $^1$H; 77.0 ppm, $^{13}$C; d$_6$-DMSO: 2.54 ppm, $^1$H; 39.5 ppm $^{13}$C).

All air- and water-sensitive reactions were performed under argon, reaction vessels were dried overnight at 80° C. in the drying cabinet. THF was freshly distilled over sodium/benzophenone, DCM was desiccated over Na$_2$SO$_4$, all other reagents and solvents were used as received.

| Abbreviations | |
|---|---|
| AcOEt | ethyl acetate |
| DCM | dichloromethane |
| h | hour |
| Hex | hexane |
| LR-MS | low resolution mass spectrometry |
| MeCN | acetonitrile |
| MeOH | methanol |
| min | minute |
| MS | mass spectrometry |
| NMR | nuclear magnetic resonance |

-continued

| Abbreviations | |
|---|---|
| PDA | photodiode array |
| PPh$_3$ | triphenyl phosphine |
| RP | reverse phase |
| sh | shoulder |
| THF | Tetrahydrofurane |
| TFA | trifluoroacetic acid |
| UPLC | ultra high-performance liquid chromatography |
| UV | ultra-violet |
| Vis | Visible |
| tr | retention time |

Synthesis Protocols

The products consist of a variable portion and a constant, alkylated or fluorinated portion connected by an ethylene bridge. The same three-step general procedure was used for the preparation of all products: a protected aryl bromide corresponding to the variable portion was converted in the corresponding styrene via Suzuki cross-coupling using potassium vinyltrifluoroborate as a vinyl source (step I); the styrene derivative was hydroborated and then employed for a Suzuki sp$^2$-sp$^3$ cross-coupling onto either the alkylated or the fluorinated constant portion as an aryl bromide (step II); the resulting protected product was deacetylated by saponification (step III), yielding the free product. General synthesis procedures for the three steps are given in the subsection below.

Products having one asymmetric center were obtained as racemates, products having several asymmetric centers were obtained as mixtures of diastereomers. No attempts were made to preparatively separate the diastereomers; in case separation of the diastereoisomer signals occurred on the analytical instruments the approximate signal ratio is provided.

General Synthesis Procedure

Step I: vinylation (adapted from a literature procedure)
G. A. Molander, A. R. Brown, J. Org. Chem., 71, 9681 (2006).

The protected aryl bromide, potassium vinyltrifluoroborate (1.00 eq), Cs$_2$CO$_3$ (3.00 eq) and PPh$_3$ (0.06 eq) were given in a pressure-tight reactor, 0.02 eq of a 10 mM PdCl$_2$ solution in THF/H$_2$O 9:1 were added, the reactor was closed tightly and heated to mild reflux under magnetic stirring overnight. The mixture was diluted with H$_2$O (3 mL/mmol aryl bromide), extracted in AcOEt (2×4.5 mL/mmol), washed with brine (4.5 mL/mmol), dried on Na$_2$SO$_4$ and concentrated under reduced pressure. The crude product was purified by preparative RP-HPLC; after purification, the resulting styrene was added with 0.01 eq 2,6-di-tert-butyl-4-methylphenol and stored under argon at 18° C. to prevent spontaneous polymerization.

Step II: sp2-sp3 cross-coupling (adapted from a literature procedure)
A. Fürstner, A. Leitner, Synlett, 2, 290 (2001).

The styrene obtained in step I (1.33 eq) was given in a reaction glass, which was evacuated and put under Ar pressure (3×). 0.67 eq 9-bora-[3.3.1]-bicyclononane dimer and THF (2.0 mL/mmol aryl bromide coupling partner) were added and the mixture was stirred at room temperature. After 5 h potassium methylate (1.34 eq) was added. The aryl bromide coupling partner was diluted in THF (0.5 mL/mmol aryl bromide) and added to the reaction mixture. Palladium (II) acetate (0.03 eq) and 1,3-bis-(2,6-di-isopropyl-phenyl)-imidazolium chloride (0.06 eq) were given in a separate flask, THF (2.0 mL/mmol aryl bromide) was added and after stirring for 15 min at room temperature the resulting solution was added to the reaction mixture, which was then heated to mild reflux. After 2.5 h the mixture was cooled to room temperature and filtered over a celite pad, which was rinsed with several portions of THF. The mother liquors were concentrated under reduced pressure, taken-up in DCM (35 mL/mmol aryl bromide), washed with H$_2$O (12 mL/mmol aryl bromide), the aqueous phase was back-extracted with DCM (2×6 mL/mmol aryl bromide), the pooled organic phases were washed with 15% NH$_4$Cl (16 mL/mmol aryl bromide), dried over Na$_2$SO$_4$ and concentrated under reduced pressure. The crude protected product was purified by flash-chromatography (Hex/AcOEt).

Step III: Final Deprotection

The protected product obtained in step II was dissolved in MeOH (15 mL/mmol) and cooled to 0° C. under Ar. LiOH*H$_2$O (3 eq) was dissolved in H$_2$O (0.2 mL/mL MeOH) and added to the protected product solution under stirring. After saponification was completed, as judged by UPLC analysis, about half of the mixture was removed under reduced pressure and the residue taken up in AcOEt (4 mL/mL MeOH) and 5% NaHCO$_3$ (2 mL/mL MeOH). The aqueous phase was extracted with AcOEt (1 mL/mL MeOH), the pooled organic extracts were washed with 5% NaHCO$_3$ (2 mL/mL MeOH) and brine (2 mL/mL MeOH), dried over Na$_2$SO$_4$, concentrated under reduced pressure, taken-up with DCM and evaporated to dryness under reduced pressure.

Example 1: Compound According to the Formula I-a 1-(4-(3-((3E,5E)-7-ethyl-7-hydroxynona-3,5-dien-3-yl)phenethyl)phenyl)butane-1,3-diol Step I From 962 mg 1,3-diacetoxy-1-(4'-bromophenyl)-butane (2.91 mmol) and 402 mg potassium vinyltrifluoroborate (2.91 mmol) 533 mg 1,3-diacetoxy-1-(4'-styryl)-butane (V8P) were obtained as an oil after preparative HPLC purification (65% yield).

Characterization

Analytical UPLC (0-100% B in A in 1.5 min, 100% B 1.5-2.5 min): 1.58 min (major diasteromer), 1.60 (minor diastereomer). Signal ratio: 2:1.

Analytical UPLC-MS (0-100% B' in A' in 1.5 min, 100% B' 1.5-2.5 min): 1.54 min (major diastereomer), 1.56 (minor diastereomer). Signal ratio: 2:1.

LR-MS (major diastereomer): m/z 217.2 ([M−AcO]+, clc 217.11).

Step II

From 375 mg V8P (1.33 mmol) and 348 mg (4E,6E)-7-(3'-bromophenyl)-3-ethyl-nona-4,6-dien-3-ol (LOH, 93%, 1.0 mmol) 302 mg 1-(4'-(1",3"-diacetoxybutyl)-phenyl)-2-(3'-((4"E,6"E)-3"-ethyl-nona-4",6"-dien-3"-ol-7"-yl)-phenylyethane (I-aAc) were obtained as an oil after flash-chromatographic purification in Hex/AcOEt 4:1 to 3:1 (57% yield).

Characterization

Analytical UPLC (0-100% B in A in 1.5 min, 100% B 1.5-2.5 min): 1.98 min (major diastereomer), 2.01 min (minor diastereomer). Signal ratio: 2:1.

Analytical UPLC-MS (0-100% B' in A' in 1.5 min, 100% B' 1.5-2.5 min): 1.92 min (major diastereomer), 1.95 min (minor diastereomer). Signal ratio: 2:1.

LR-MS (major diastereomer): m/z 543.4 ([M+Na]+, clc 543.31).

Step III

From 300 mg I-aAc (0.56 mmol) and 71 mg LiOH*H$_2$O (1.69 mmol) 246 mg of the title compound I-a were obtained as an oil (95% yield).

Characterization

Analytical UPLC (0-100% B in A in 1.5 min, 100% B 1.5-2.5 min): 1.74 min (minor diastereomer), 1.77 min (major diastereomer). Signal ratio: 3:7.

Analytical UPLC-MS (0-100% B' in A' in 1.5 min, 100% B' 1.5-2.5 min): 1.70 min (minor diastereomer), 1.72 min (major diastereomer). Signal ratio: 1:3.

LR-MS (major diastereomer): m/z 459.4 ([M+Na]$^+$, clc 459.29).

Example 2: Compound According to the Formula I-b 1-(4-(3-((3E,5E)-8,8,8-trifluoro-7-hydroxy-7-(trifluoromethyl)octa-3,5-dien-3-yl)phenethyl)phenyl)propane-1,3-diol Step I From 2.01 g 1,3-diacetoxy-1-(4'-bromophenyl)-propane (6.0 mmol) and 828 mg potassium vinyltrifluoroborate (6.0 mmol) 877 mg 1,3-diacetoxy-1-(4'-styryl)-propane (V7P) were obtained as an oil after preparative HPLC purification (55% yield).

Characterization

Analytical UPLC (0-100% B in A in 1.5 min, 100% B 1.5-2.5 min): 1.51 min.

Analytical UPLC-MS (0-100% B' in A' in 1.5 min, 100% B' 1.5-2.5 min): 1.49 min.

LR-MS: m/z 326.0 ([M+Na+MeCN]$^+$, clc 326.14).

Step II

From 325 mg V7P (1.21 mmol) and 363 mg (3E,5E)-6-(3'-bromophenyl)-1,1,1-trifluoro-2-trifluoromethyl-octa-3,5-dien-2-ol (FOH, 0.90 mmol) 103 mg 1-(4'-(1",3"-diacetoxypropyl)-phenyl)-2-(3'-((3"E,5"E)-1",1",1"-trifluoro-2"-trifluoromethyl-octa-3",5"-dien-2"-ol-6"-yl)-phenyl)-ethane (I-bAc) were obtained as an oil after flash-chromatographic purification in Hex/AcOEt 4:1 to 3:1 (18% yield).

Characterization

Analytical UPLC (0-100% B in A in 1.5 min, 100% B 1.5-2.5 min): 1.87 min.

Analytical UPLC-MS (0-100% B' in A' in 1.5 min, 100% B' 1.5-2.5 min): 1.84 min.

LR-MS: m/z 609.5 ([M+Na]$^+$, clc 609.21).

Step III

From 102 mg 1-bAc (0.16 mmol) and 21 mg LiOH*H$_2$O (0.49 mmol) 85 mg of the title compound I-b were obtained as a thick oil (99% yield).

Characterization

Analytical UPLC (0-100% B in A in 1.5 min, 100% B 1.5-2.5 min): 1.65 min.

Analytical UPLC-MS (0-100% B' in A' in 1.5 min, 100% B' 1.5-2.5 min): 1.63 min.

LR-MS: m/z 467.3 ([M-H$_2$O—OH]$^+$, clc 467.18).

Example 3: Compound According to the Formula I-c 1-(4-(3-((3E,5E)-7-ethyl-7-hydroxynona-3,5-dien-3-yl)phenethyl)phenyl)propane-1,3-diol Step I From 2.01 g 1,3-diacetoxy-1-(4'-bromophenyl)-propane (6.0 mmol) and 828 mg potassium vinyltrifluoroborate (6.0 mmol) 877 mg 1,3-diacetoxy-1-(4'-styryl)-propane (V7P) were obtained as an oil after preparative HPLC purification (55% yield).

Characterization

Analytical UPLC (0-100% B in A in 1.5 min, 100% B 1.5-2.5 min): 1.51 min.

Analytical UPLC-MS (0-100% B' in A' in 1.5 min, 100% B' 1.5-2.5 min): 1.49 min.

LR-MS: m/z 326.0 ([M+Na+MeCN]$^+$, clc 326.14).

Step II

From 375 mg V7P (1.40 mmol) and 348 mg (4E,6E)-7-(3'-bromophenyl)-3-ethyl-nona-4,6-dien-3-ol (LOH, 93%, 1.0 mmol) 286 mg 1-(4'-(1",3"-diacetoxypropyl)-phenyl)-2-(3'-((4"E,6"E)-3"-ethyl-nona-4",6"-dien-3"-ol-7"-yl)-phenyl)-ethane (I-cAc) were obtained as an oil after flash-chromatographic purification in Hex/AcOEt 4:1 to 3:1 (55% yield).

Characterization

Analytical UPLC (0-100% B in A in 1.5 min, 100% B 1.5-2.5 min): 1.93 min.

Analytical UPLC-MS (0-100% B' in A' in 1.5 min, 100% B' 1.5-2.5 min): 1.90 min.

LR-MS: m/z 529.5 ([M+Na]$^+$, clc 529.29).

Step III

From 285 mg 1-cAc (0.55 mmol) and 70 mg LiOH*H$_2$O (1.65 mmol) 237 mg of the title compound I-c were obtained as a thick oil (quantitative yield).

Characterization

Analytical UPLC (0-100% B in A in 1.5 min, 100% B 1.5-2.5 min): 1.67 min.

Analytical UPLC-MS (0-100% B' in A' in 1.5 min, 100% B' 1.5-2.5 min): 1.64 min.

LR-MS: m/z 445.5 ([M+Na]$^+$, clc 445.27).

Example 4: Compound According to the Formula I-d 1-(4-(3-((3E,5E)-7-ethyl-7-hydroxynona-3,5-dien-3-yl)phenethyl)phenyl)-2-methylpropane-1,3-diol Step I From 1.01 g 1,3-diacetoxy-1-(4'-bromophenyl)-2-methyl-propane (3.0 mmol) and 414 mg potassium vinyltrifluoroborate (3.0 mmol) 446 mg 1,3-diacetoxy-1-(4'-styryl)-2-methylpropane (V9P) were obtained as an oil after preparative HPLC purification (51% yield, according to NMR the derivative contained about 4% starting material).

Characterization

Analytical UPLC (0-100% B in A in 1.5 min, 100% B 1.5-2.5 min): 1.54 min.

Analytical UPLC-MS (0-100% B' in A' in 1.5 min, 100% B' 1.5-2.5 min): 1.48 min.

LR-MS: m/z 217.2 ([M−AcO]$^+$, clc 217.11), 340.2 ([M+Na+MeCN]$^+$, clc 340.17).

Step II

From 387 mg V9P (containing about 4% starting material, 1.33 mmol) and 348 mg (4E,6E)-7-(3'-bromophenyl)-3-ethyl-nona-4,6-dien-3-ol (LOH, 93%, 1.0 mmol) 298 mg 1-(4'-(1",3"-diacetoxy-2"-methylpropyl)-phenyl)-2-(3'-((4"E,6"E)-3"-ethyl-nona-4",6"-dien-3"-ol-7"-yl)-phenyl)-ethane (I-dAc) were obtained as an oil after flash-chromatographic purification in Hex/AcOEt 4:1 to 3:1 (57% yield).

Characterization

Analytical UPLC (0-100% B in A in 1.5 min, 100% B 1.5-2.5 min): 1.94 min.

Analytical UPLC-MS (0-100% B' in A' in 1.5 min, 100% B' 1.5-2.5 min): 1.96 min.

LR-MS: m/z 503.4 ([M−OH]+, clc 503.32) 543.3 ([M+Na]⁺, clc 543.31).

Step III

From 297 mg I-dAc (0.56 mmol) and 71 mg LiOH*H₂O (1.69 mmol) 247 mg of the title compound I-d were obtained as an oil (97% yield).

Characterization

Analytical UPLC (0-100% B in A in 1.5 min, 100% B 1.5-2.5 min): 1.75 min (minor diastereomer), 1.77 min (major diastereomer). Signal ratio: 1:4.

Analytical UPLC-MS (0-100% B' in A' in 1.5 min, 100% B' 1.5-2.5 min): 1.73 min.

LR-MS: m/z 419.4 ([M−OH]⁺, clc 419.30), 459.4 ([M+Na]⁺, clc 459.29).

Example 5: Compound According to the Formula I-e 1-(4-(3-((3E,5E)-7-ethyl-7-hydroxynona-3,5-dien-3-yl)phenethyl)phenyl)-2-(hydroxymethyl)pentane-1,5-diol Step I From 650 mg 1,5-diacetoxy-1-(4'-bromophenyl)-2-acetoxymethylpentane (1.53 mmol) and 211 mg potassium vinyltrifluoroborate (1.53 mmol) 445 mg 1,5-diacetoxy-1-(4'-styryl)-2-acetoxymethylpentane (V11P) were obtained as an oil after flash-chromatographic purification in Hex/AcOEt 2:1 to 1:1 (67% yield, according to NMR the derivative contained about 15% starting material).

Characterization

Analytical UPLC (0-100% B in A in 1.5 min, 100% B 1.5-2.5 min): 1.55 min.

Analytical UPLC-MS (0-100% B' in A' in 1.5 min, 100% B' 1.5-2.5 min): 1.53 min.

LR-MS: m/z 385.3 ([M+Na]⁺, clc 385.16).

Step II

From 440 mg V11P (containing about 15% starting material, 1.01 mmol) and 348 mg (4E,6E)-7-(3'-bromophenyl)-3-ethyl-nona-4,6-dien-3-ol (LOH, 93%, 1.0 mmol) 245 mg 1-(4'-(1",5"-diacetoxy-2"-acetoxymethylpentyl)-phenyl)-2-(3'-((4"E,6"E)-3"-ethyl-nona-4",6"-dien-3"-ol-7"-yl))-phenyl)-ethane (I-eAc) were obtained as an oil after flash-chromatographic purification in Hex/AcOEt 3:1 to 2:1 (39% yield).

Characterization

Analytical UPLC (0-100% B in A in 1.5 min, 100% B 1.5-2.5 min): 1.94 min.

Analytical UPLC-MS (0-100% B' in A' in 1.5 min, 100% B' 1.5-2.5 min): 1.90 min.

LR-MS: m/z 589.6 ([M−OH]⁺, clc 589.35), 629.4 ([M+Na]⁺, clc 629.35).

Step III

From 244 mg 1-eAc (0.39 mmol) and 66 mg LiOH*H₂O (1.56 mmol) 168 mg of the title compound I-e were obtained as an oil (88% yield).

Characterization

Analytical UPLC (0-100% B in A in 1.5 min, 100% B 1.5-2.5 min): 1.61 min.

Analytical UPLC-MS (0-100% B' in A' in 1.5 min, 100% B' 1.5-2.5 min): 1.58 min.

LR-MS: m/z 463.4 ([M−OH]⁺, clc 463.32), 503.5 ([M+Na]⁺, clc 503.31).

Example 6: Compound According to the Formula I-f 1-(4-{2-[3-((1E,3E)-1,5-Diethyl-5-hydroxy-hepta-1,3-dienyl)-phenyl]-ethyl}-phenyl)-2-methylbutane-1,3-diol Step I From 670 mg 1,3-diacetoxy-1-(4'-bromophenyl)-2-methylbutane (1.93 mmol) and 266 mg potassium vinyltrifluoroborate (1.93 mmol) 347 mg 1,3-diacetoxy-1-(4'-styryl)-2-methylbutane (V10P) were obtained as an oil after preparative HPLC purification (61% yield).

Characterization

Analytical UPLC (0-100% B in A in 1.5 min, 100% B 1.5-2.5 min): 1.64 min (minor), 1.67 min (major). Signal ratio: 2:3.

Analytical UPLC-MS (0-100% B' in A' in 1.5 min, 100% B' 1.5-2.5 min): 1.62 min (minor), 1.64 min (major). Signal ratio: 1:2.

LR-MS (major signal): m/z 345.3 ([M+Na+MeCN]⁺, clc 345.17).

Step II

From 340 mg V10P (1.16 mmol) and 348 mg (4E,6E)-7-(3'-bromophenyl)-3-ethyl-nona-4,6-dien-3-ol (LOH, 93%, 1.0 mmol) 308 mg 1-(4'-(1",3"-diacetoxy-2"-methylbutyl)-phenyl)-2-(3'-((4"E,6"E)-3"-ethyl-nona-4",6"-dien-3"-ol-7"-yl)-phenyl)-ethane (I-fAc) were obtained as an oil after flash-chromatographic purification in Hex/AcOEt 4:1 to 3:1 (57% yield).

Characterization

Analytical UPLC (0-100% B in A in 1.5 min, 100% B 1.5-2.5 min): 2.03 min (minor signal), 2.06 min (major signal). Signal ratio: 2:3.

Analytical UPLC-MS (0-100% B' in A' in 1.5 min, 100% B' 1.5-2.5 min): 1.98 min (minor signal), 2.00 min (major signal). Signal ratio: 1:2.

LR-MS (major signal): m/z 557.44 ([M+Na]⁺, clc 557.32).

Step III

From 307 mg 1-fAc (0.56 mmol) and 71 mg LiOH*H₂O (1.69 mmol) 228 mg of the title compound I-f were obtained as an oil (95% yield).

Characterization

Analytical UPLC (0-100% B in A in 1.5 min, 100% B 1.5-2.5 min): 1.84 min.

Analytical UPLC-MS (0-100% B' in A' in 1.5 min, 100% B' 1.5-2.5 min): 1.80 min.

LR-MS: m/z 433.4 ([M−OH]⁺, clc 433.31), 473.5 ([M+Na]⁺, clc 473.30).

Comparative Example 1

Compound according to formula (Comp1)—not according to the present invention:

Formula (Comp 1)

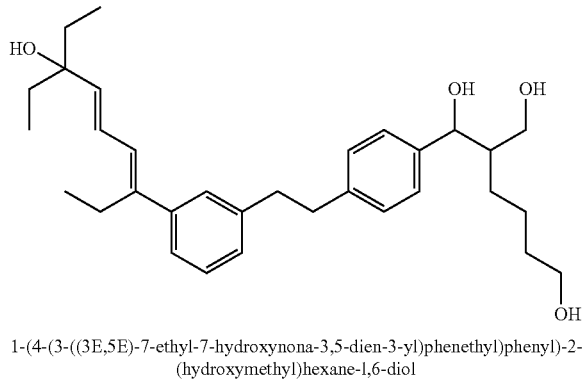

1-(4-(3-((3E,5E)-7-ethyl-7-hydroxynona-3,5-dien-3-yl)phenethyl)phenyl)-2-(hydroxymethyl)hexane-1,6-diol Step I From 630 mg 1,6-diacetoxy-1-(4'-bromophenyl)-2-acetoxymethylhexane (1.46 mmol) and 202 mg potassium vinyltrifluoroborate (1.46 mmol) 308 mg 1,6-diacetoxy-1-(4'-styryl)-2-acetoxymethylhexane (V12P) were obtained as an oil after preparative HPLC purification (55% yield). According to NMR the diastereomeric ratio was 4:1.

Characterization

Analytical UPLC (0-100% B in A in 1.5 min, 100% B 1.5-2.5 min): 1.61 min.

Analytical UPLC-MS (0-100% B' in A' in 1.5 min, 100% B' 1.5-2.5 min): 1.59 min.

LR-MS (major signal): m/z 399.3 ([M+Na]$^+$, clc 399.18).

Step II

From 300 mg V12P (0.79 mmol) and 266 mg (4E,6E)-7-(3'-bromophenyl)-3-ethyl-nona-4,6-dien-3-ol (LOH, 93%, 0.77 mmol) 87 mg 1-(4'-(1'',6''-diacetoxy-2''-acetoxymethylhexyl)-phenyl)-2-(3'-((4''E,6''E)-3''-ethyl-nona-4'',6''-dien-3''-ol-7''-yl)-phenyl)-ethane (Comp1Ac) were obtained as an oil after flash-chromatographic purification in Hex/AcOEt 3:1 to 2:1 (17% yield).

Characterization

Analytical UPLC (0-100% B in A in 1.5 min, 100% B 1.5-2.5 min): 1.98 min.

Analytical UPLC-MS (0-100% B' in A' in 1.5 min, 100% B' 1.5-2.5 min): 1.94 min.

LR-MS: m/z 589.6 ([M−OH]$^+$, clc 589.35), 629.4 ([M+Na]$^+$, clc 629.35).

Step III

From 83 mg Comp1Ac (0.12 mmol) and 21.5 mg LiOH*H$_2$O (0.50 mmol) 56 mg of the title compound I-e were obtained as an oil (92% yield).

Characterization

Analytical UPLC (0-100% B in A in 1.5 min, 100% B 1.5-2.5 min): 1.65 min.

Analytical UPLC-MS (0-100% B' in A' in 1.5 min, 100% B' 1.5-2.5 min): 1.61 min.

LR-MS: m/z 517.5 ([M+Na]$^+$, clc 517.32).

Comparative Example 2

The compound according to Example 1 of US 2004/0224929 A1 was prepared (Comp2), as this compound is structurally close to the compounds according to the present invention.

Testing of the Human Vitamin D Receptor (VDR) Agonist Activity of the Compounds

The activities of all example compounds—those according to the invention and those according to the comparative examples—have been tested as follows.

The transient transfections were performed in HEK293 cells (ATCC, Molsheim, France) grown in minimum essential medium (Eagle) with Earle's balanced salt solution without L-glutamine and supplemented with 10% fetal bovine serum (Sigma-Aldrich Corp., St. Gallen, Switzerland), 2 mM glutamax (Life Technologies AG, Basel, Switzerland), 0.1 mM non-essential amino acids (Life Technologies), and 1 mM sodium pyruvate (Life Technologies) at 37° C. in 5% $CO_2$. For transfection, 7.5×104 cells were plated per well (80 µl) in white 96-well cell culture plates with clear bottom (Corning, Basel, Switzerland) in minimum essential medium (Eagle) with Earle's balanced salt solution without L-glutamine and without phenol red supplemented with 10% charcoal-treated fetal bovine serum (HyClone Laboratories, Inc., Logan, Utah, USA), 2 mM glutamax, 0.1 mM non-essential amino acids, and 1 mM sodium pyruvate. The cells were transiently transfected before stimulation the next day at >80% confluence by polyethylene-imine-based transfection. Compound stocks were prepared in DMSO, pre-diluted in PBS (0.45% final DMSO concentration), and added in the respective dilution 5 h after the addition of the transfection mixture onto the cells. The cells were again incubated for additional 16 h before firefly and renilla luciferases activity was measured sequentially in the same cell extract using buffers according to established protocols (Promega AG, Dübendorf, Switzerland). Transfection efficiency was controlled to the pRL-TK renilla luciferase reporter expression. The ligand-binding domain of VDR was expressed from a GATEWAY (Invitrogen, Zug, Switzerland)-compatible version of pCMV-BD (Stratagene Corp., Santa Clara, Calif., USA) as a fusion to the GAL4 DNA-binding domain (amino acids 1 to 147). pFR-Luc (Stratagene) was used as a reporter plasmid to determine the VDR agonist binding and transactivation.

Results

The results are given in table 1:

TABLE 1

| Effective concentrations of half maximal activation (EC$_{50}$) | |
|---|---|
| compound | EC$_{50}$ (nM) |
| 1,25 dihydrocholecalciferol (control) | 0.65 |
| Comp1 | 111 |
| Comp2 | 74 |
| I-a | 4 |
| I-b | 12 |
| I-c | 13 |
| I-d | 28 |
| I-e | 30 |
| I-f | 34 |

The results show the surprisingly much stronger activity of the compounds of the invention with respect to the comparative compounds Comp1 and Comp2.

Example 4: Cosmetic Composition

Table 2 outlines exemplary O/W emulsions, wherein one (or more) compound(s) according to the formulas I-a, I-b and/or I-c is (are) incorporated in the indicated amount (in wt.-%, based on the total weight of the composition).

TABLE 2

Exemplary O/W emulsion

| O/W Emulsions | 1 | 2 | 3 | 4 | 5 | 6 | 7 | 8 |
|---|---|---|---|---|---|---|---|---|
| Glyceryl Stearate | 2.5 | 2 | 1.2 | 1 | | | 1 | 1 |
| PEG-40 Stearate | 1 | | | | | | | |
| PEG-100 Stearate | | 2.5 | | | | | | 1 |
| Ceteareth-20 | | | | | 1 | | | |
| Glyceryl Stearate Citrate | | | | | | 0.5 | | |
| Potassium Cetyl Phosphate | | | | | | | 3 | 1.5 |
| Stearic Acid | | | 2.5 | 3 | | | | |
| Cetearyl Alcohol | 4 | | | 2 | | | 2 | |
| Stearyl Alcohol | | 2 | 1 | | | | | |
| Cetyl Alcohol | | | 1 | 1 | | | | 0.5 |
| Acrylates/$C_{10-30}$ Alkyl Acrylate Crosspolymer | | | | 0.2 | 0.2 | 0.4 | 0.2 | |
| Carbomer | 0.1 | | 0.2 | | | | | |
| Xanthan Gum | | 0.3 | | | | | | 0.3 |
| $C_{12-15}$ Alkyl Benzoate | 5 | | | 2 | 5 | 5 | 10 | 5 |
| Petrolatum | 5 | | 3 | | | | | |
| Butylene Glycol | | 4 | 2 | | 9 | | | 9 |
| Dicaprylate/Dicaprate | | | | | | | | |
| Hydrogenated Polydecene | | | 3 | | 2 | | | 2 |
| Caprylic/Capric Triglyceride | 1 | 3 | | 5 | | 5 | 5 | |
| Cyclomethicone | | 5 | 2 | | | 10 | | |
| Methylpropanediol | 2 | | | | 3 | | | 3 |
| Glycerine | 4 | 7 | 3 | 4 | 3 | | 5 | 3 |
| Glyceryl Glucoside | 3.5 | 3 | 1 | 1 | 2 | | | 2 |
| Alcohol denat. | 1 | 3 | 0.5 | 10 | 4 | 8 | | 4 |
| Butylene Glycol | | | 3 | | | | | |
| Ascorbylglucoside | | 0.5 | | 1.0 | | 1.5 | | 0.1 |
| Ubiquinone (Coenzyme 10) | 0.1 | | 0.05 | | | | 0.01 | |
| Hyaluronic acid | | | | | 0.2 | | | |
| Bisabolol | 0.5 | | | | | | 0.2 | |
| Isotridecylsalicylate | | | 1 | 3 | 5 | 2 | 3 | 5 |
| Compound (1-a) | 0.00001 | | | | | 0.00002 | | 0.002 |
| Compound (1-b) | | | 0.0001 | | | | 0.03 | |
| Compound (1-c) | | | | | 0.1 | | | |
| Compound (1-d) | | 0.025 | | | | | | |
| Compound (1-e) | | | | | 0.05 | | | |
| Compound (1-f) | | | | | | 0.00005 | | |
| Dibutyl Adipate | 1.5 | 3 | | | | | | |
| Diisopropyl sebacate | | | 1 | 1 | 2 | 3 | | |
| Ethylhexyl Benzoate | | | | | | 0.75 | 1.5 | 1 |
| Titanium Dioxide (PARSOL TX) | | | 0.5 | 2 | | | | |
| Methylene Bis-Benztriazoyl Tetramethylbutylphenol | | | 0.5 | 4 | | 6 | | 2 |
| Ethylhexyl methoxycinnamate | | | | | 2 | | | |
| Phenylbenzimidazole Sulfonic Acid | | | | 2 | | 2 | 2 | |
| Butyl Methoxydibenzoylmethane | | 1 | | 2 | 2 | 3 | 3 | 3 |
| Methylbenzylidene Camphor | | | | | 2 | 3 | | |
| Octocrylene | | 5 | | | | 2 | 10 | |
| Polysilicone-15 | | | | 2 | | 3 | | |
| Ethylhexyl Salicylate | | | | | 5 | | | |
| Homosalate | | | | 4 | 2 | | | |
| Bis-Ethylhexyloxyphenol Methoxyphenyltriazine | | 1.5 | | | | | | 2 |
| Silica | 1 | | 2.5 | | | 0.5 | | |
| Silica & Methicone | | 4 | | 1 | 2.5 | | | |
| Methyl Methacrylate Crosspolymer | | | | 1 | | | 2 | |
| Disodium EDTA | 0.1 | | | | | 0.5 | | |
| Fragrance, Preservatives | | | | q.s. | | | | |
| Sodium Hydroxide | | | | q.s. | | | | |
| Water | | | | Ad 100 | | | | |

The invention claimed is:

1. A compound according to formula (I):

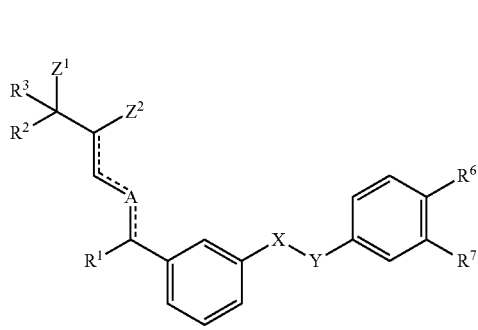

wherein

X and Y, are either both —CH$_2$—, or one of X and Y is —CH$_2$— and the other is —O—;

R$^1$ is a methyl group or an ethyl group;

A is either a carbon atom, CH group, CH$_2$ group or an oxygen atom;

one of Z$^1$ and Z$^2$ represents a hydroxyl group and the other one is a hydrogen atom;

R$^2$ and R$^3$, independently of each other, represent a hydrogen atom, a methyl group, an ethyl group, or a CF$_3$ group or R$^2$ and R$^3$, together with the carbon they are bound to, form a cyclopropyl group;

the dotted/solid lines ( ----- ) represent either a single carbon-carbon bond or a double carbon-carbon bond, with the proviso that, if two of said bonds are double bonds, the double bonds are conjugated;

one of R$^6$ and R$^7$ represents a hydrogen atom and the other one represents a radical R$^8$, wherein

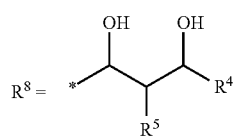

wherein R$^4$ represents a hydrogen atom, a methyl group, an ethyl group, a propyl group, a (CH$_2$)$_n$OR$^9$ group where n is 1, 2, 3 or 4; and R$^5$ represents a hydrogen atom, a methyl group, an ethyl group, a propyl group, or a (CH$_2$)$_n$OR$^{10}$ group where n is 1, 2 or 3, and wherein R$^9$ and R$^{10}$, independently of each other, represent a hydrogen atom, a methyl group, or an ethyl group.

2. The compound according to claim 1, wherein R$^1$ is ethyl.

3. The compound according to claim 1, wherein R$^2$, R$^3$ independently of each other represent an ethyl group, or a CF$_3$ group.

4. The compound according to claim 1, wherein R$^4$ and R$^5$ are different and represent a hydrogen atom and a methyl group.

5. A compound according to formula (I-a):

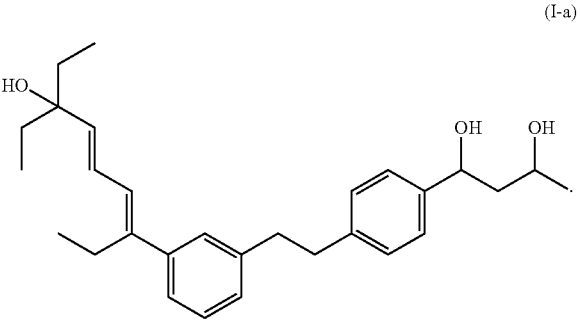

6. A compound according to formula (I-b):

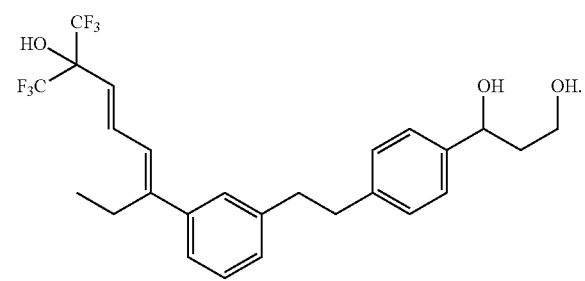

7. A compound according to formula (I-c):

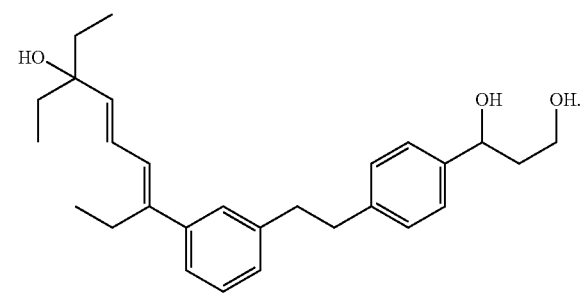

8. A compound according to formula (I-d):

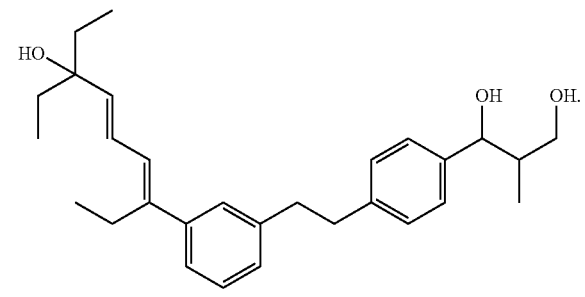

9. A compound according to formula (I-e):

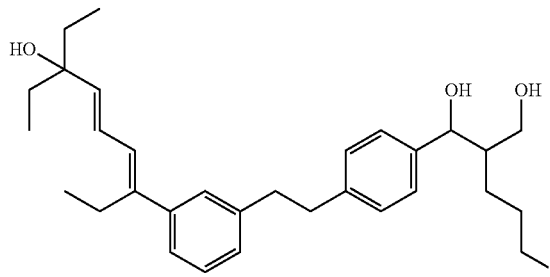

(I-e)

10. A compound according to formula (I-f):

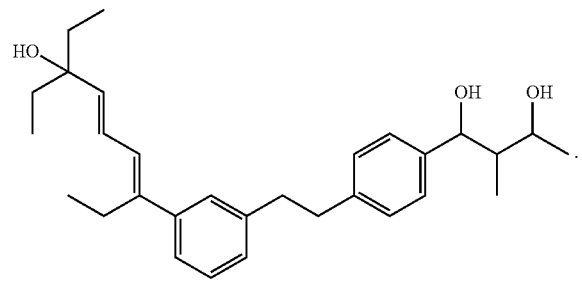

(I-f)

11. A cosmetic composition comprising the compound according to claim 1.

12. The cosmetic composition according to claim 11, wherein the compound of formula (I) is present in an amount in the range of 0.00001 to 0.1 wt.-%, based on the total weight of the cosmetic composition.

13. A method to smooth skin wrinkles and/or fine lines and/or to decrease volume and depth thereof, wherein the method comprises a step of applying the cosmetic composition according to claim 11 to an affected area of skin containing wrinkles and/or fine lines.

14. A dermatological composition comprising one or more of the compounds according to claim 1.

15. A pharmaceutical composition comprising one or more of the compounds according to claim 1.

16. A process for preparing the compound of claim 1, which comprises a step of hydroboration of a styrene-containing moiety to form an organoborane, followed by conducting a $sp^2$-$sp^3$ Suzuki cross coupling of the organoborane with an aryl halogenide to form a 1,2 diphenylethane core structure.

* * * * *